(12) United States Patent
Pedersen et al.

(10) Patent No.: US 6,639,237 B2
(45) Date of Patent: Oct. 28, 2003

(54) BRACHYTHERAPY MEDICAL DEVICES

(75) Inventors: Laust Pedersen, Santa Barbara, CA (US); Jerry Barber, Ventura, CA (US); Ronald Crouther, Camarillo, CA (US); Dennis Femrite, Andover, MN (US); Scott Henderson, Palm Harbor, FL (US); Charles Pitman, Santa Barbara, CA (US); Martin T. Steele, Sr., Otsego, MN (US)

(73) Assignee: Mentor Corporation, Santa Barbara, CA (US)

( * ) Notice: Subject to any disclaimer, the term of this patent is extended or adjusted under 35 U.S.C. 154(b) by 0 days.

(21) Appl. No.: 10/008,372

(22) Filed: Nov. 2, 2001

(65) Prior Publication Data

US 2003/0088143 A1 May 8, 2003

(51) Int. Cl.⁷ .................................................. G21F 5/00
(52) U.S. Cl. .............................. 250/506.1; 600/3; 600/7
(58) Field of Search ........................... 250/506.1; 600/3, 600/7

(56) References Cited

U.S. PATENT DOCUMENTS 3,801,279 A * 4/1974 Grieco ........................ 21/87
4,759,345 A * 7/1988 Mistry ........................ 128/1.2
6,358,195 B1 * 3/2002 Green et al. .................. 600/7

OTHER PUBLICATIONS

U.S. patent application Ser. No. 09/792,307.

* cited by examiner

*Primary Examiner*—John R. Lee
*Assistant Examiner*—Phillip A Johnston
(74) *Attorney, Agent, or Firm*—Fish & Richardson P.C., P.A.

(57) ABSTRACT

The invention relates to brachytherapy devices, methods for making brachytherapy devices, and methods for using brachytherapy devices. For example, the invention provides brachytherapy devices such as staging-sterilization devices and insert devices that can be used in various brachytherapy procedures.

43 Claims, 18 Drawing Sheets

BRACHYTHERAPY MEDICAL DEVICES

BACKGROUND

1. Technical Field

This invention relates to medical devices, and more particularly to medical devices useful for brachytherapy procedures.

2. Background Information

Brachytherapy is a form of cancer treatment in which radiation sources are placed inside a patient's body to irradiate a tumor. In brachytherapy, a surgeon usually implants several radioactive seeds in or around a tumor, thus providing a higher radiation dose to the tumor than would be possible with external beam radiation therapy. Careful placement of the radioactive seeds allows localized and precise irradiation of the tumor. Because the radiation dose diminishes rapidly outside the radioactive seed, the radiation dose to surrounding healthy tissues is minimized.

Radioactive seeds typically are tiny (generally about 0.8 mm by 4.5 mm), roughly cylindrical objects containing very small amounts of radioactive material. In one widely practiced brachytherapy procedure, the radioactive seeds are implanted permanently inside the patient's body. The half-life of the radioactive material is generally short, and the radioactivity in the seeds decays after about three to six months to the point that there is little detectable radiation. Two radioactive isotopes commonly used for permanent implants are iodine-125, often used to treat slower growing tumors, and palladium-103, which is preferred when a tumor is fast growing. Other radioactive materials have been used in implants as well.

Many forms of cancer respond to brachytherapy, including several forms of prostate cancer. Brachytherapy is generally less invasive than surgery, usually results in fewer side effects than surgery or external beam radiation, allows for a shorter recovery time, and reduces the impact on the patient's quality of life.

SUMMARY

The invention relates to brachytherapy devices, methods for making brachytherapy devices, and methods for using brachytherapy devices. Specifically, the invention provides staging-sterilization devices and insert devices. Staging-sterilization devices can have a staging area with a loading area that can be used to secure a seed holder such that a practitioner can load the seed holder with radioactive seeds. The loading area can be configured to secure the seed holder in five of six degrees of freedom. For example, the loading area can be configured to restrict or prevent side to side as well as up-down movements of the seed holder. In addition, the loading area can be configured such that a secured seed holder can be removed from the loading area by pivoting the seed holder around its transverse axis through its base followed by a translation along its longitudinal axis. The pivoting movement can have an angular range from zero to ten degrees with an angle of five to ten degrees being needed to allow removal of the seed holder via the translation. Such a configuration can allow the practitioner to load a seed holder with confidence that any accidental pressures applied to the seed holder will not dislodge the seed holder. Thus, the loading areas provided herein can prevent accidental movements of a seed holder. Preventing accidental movements of a seed holder protects practitioners from unnecessary exposure to radioactivity.

The staging-sterilization devices provided herein also can have a staging area configured such that any radioactive seeds dropped over the staging area collect in a trough. This allows the practitioner to locate dropped radioactive seeds quickly. Locating a dropped radioactive seed in a trough can prevent practitioners from having to search a large area such as the floor. In addition, having dropped radioactive seeds collect in a trough can prevent exposure to radioactivity that may otherwise occur if the dropped radioactive seed rolls outside the shielded work station.

In addition, the staging-sterilization devices provided herein can be used to store, transfer, and sterilize other brachytherapy components such as seed holders, radioactive seeds, and transfer devices. Such staging-sterilization devices can have at least one well and a lid such that radioactive material can be placed in the well and shielded when the lid is closed. Staging-sterilization devices can protect practitioners from unnecessary exposure to radiation and can provide a convenient vessel for organizing brachytherapy components. In addition, the staging-sterilization devices provided herein can be configured such that the components within the staging-sterilization device heat and cool quickly. In other words, staging-sterilization devices can be configured to maximize heat exchange, minimizing the amount of time needed to wait after sterilizing brachytherapy components.

The invention provides brachytherapy devices such as insert devices that can be configured to hold multiple seed holders. For example, an insert device can have seven seed holder pockets such that seven seed holders can be vertically placed into a single insert device. Insert devices can be configured to maximize heat exchange such that seed holders placed in the insert device heat and cool quickly, minimizing the amount of time between sterilization and surgical implantation of radioactive seeds.

The staging-sterilization devices and insert devices provided herein can be designed such that the insert device fits within an insert receiving well of the staging-sterilization device. In addition, the staging-sterilization devices and insert devices provided herein can be designed such that movement of the insert device and any seed holder within the insert device is restricted while within the staging-sterilization device with its lid closed. Restricting movement of the insert device and seed holders within the insert device can prevent damage to the seed holders and can prevent radioactive seeds from being dislodged from seed holders if, for example, the staging-sterilization device is accidentally dropped.

In general, the invention features a brachytherapy device containing (a) a body containing a top surface, a bottom surface, and a staging area surface, wherein the top surface contains an insert receiving well capable of holding an insert device, and wherein the staging area surface slopes away from the top surface and toward the bottom surface; and (b) a lid attached to the body, wherein the lid is capable of opening to expose the insert receiving well and is capable of closing over the top surface to cover the insert receiving well. The body can contain a vent that creates a line of sight through the body. Such a vent can extend from the top surface to the bottom surface. The body can contain a vent that does not create a line of sight through the body. Such a vent can extend from the insert receiving well to the bottom surface. The top surface can be substantially parallel with a flat surface when the bottom surface rests on the flat surface. The top surface can contain multiple insert receiving wells. The top surface can contain a transfer device well capable of holding a transfer device. The top surface can contain multiple transfer device wells. A portion of the top surface can be raised. The insert receiving well can be cylindrically shaped. The bottom of the insert receiving well can contain a pin capable of aligning the insert device. The pin can be conically shaped. The bottom of the insert receiving well can contain multiple pins capable of aligning the insert device. The bottom surface can contain a hollow bottom. At least a portion of the hollow bottom can be positioned underneath the staging area surface. The angle of the staging area with respect to a flat surface can be less than 60 degrees when the bottom surface rests on the flat surface. The angle is of the staging area with respect to a flat surface can be between 80 and 10 degrees when the bottom surface rests on the flat surface. The angle of the staging area with respect to a flat surface can be between 60 and 30 degrees when the bottom surface rests on the flat surface. The staging area surface can contain a loading area having one or more seed holder supports capable of holding a seed holder. The one or more seed holder supports can be capable of restricting longitudinal movement of the seed holder. The one or more seed holder supports can be capable of restricting latitudinal movement of the seed holder. The loading area can contain a restraining wire attached to the one or more seed holder supports, wherein the restraining wire is capable of restricting axial movement of the seed holder. The staging area can contain a top portion and a bottom portion, wherein the bottom portion contains a trough capable of collecting a radioactive seed that rolls down the top portion. The lid can be attached to the body via an integral hinge. The lid can define an interior region, wherein a portion of the interior region contains a protrusion capable of restraining movement of a seed holder within the insert device when the lid is closed. The protrusion can extend between the pick-up handles of the insert device when the lid is closed. The clearance between the protrusion and the seed holder can be less than 0.1 inches. The clearance between the protrusion and the seed holder can be less than 0.01 inches. The clearance between the protrusion and the seed holder can be less than 0.005 inches. The brachytherapy device can contain a handle attached to the body. The handle can contain a lock that locks the lid in the closed position. The lock can lock the lid in the closed position when the handle is in a vertical position. Movement of the handle from a vertical position toward a horizontal position can move the lid from a closed position to an opened position. The center of gravity of the brachytherapy device can be such that the lid closes from an open position when the brachytherapy device is lifted by the handle. The body and lid can be aluminum.

In another aspect, the invention features a brachytherapy device containing (a) multiple seed holder pockets, wherein each of the multiple seed holder pockets is capable of holding a seed holder, and (b) a pick-up handle. A connector can connect at least two of the multiple seed holder pockets. Each of the multiple seed holder pockets can contain a top portion and a bottom portion, wherein the top portion contains a cylindrical inner space, and wherein the bottom portion contains a rectangular inner space. The brachytherapy device can contain at least two pick-up handles. Each of the at least two pick-up handles can contain an aperture. The brachytherapy device can be plastic. The brachytherapy device can be capable of fitting within an insert receiving well of a staging-sterilization device. At least one of the multiple seed holder pockets can contain a vent.

Another aspect of the invention features a brachytherapy kit containing a staging-sterilization device and an insert device.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides brachytherapy devices, methods for making brachytherapy devices, and methods for using brachytherapy devices. For example, the invention provides brachytherapy devices such as staging-sterilization devices and insert devices. These devices can be used with other brachytherapy components such as radioactive seeds, seed holders, and transfer devices. Briefly, radioactive seeds can be small cylindrical objects containing radioactive material such as iodine-125 or palladium-103. Radioactive seeds that will be implanted into a patient can be assembled into seed holders, which can be cartridges having the capacity for one or more radioactive seeds. Seed holders can be constructed from clear molded plastic to allow visualization of the radioactive seeds contained within. One or more seed holders can be placed into an insert device described herein. Alternatively, a single seed holder can be placed into a transfer device for movement from a staging-sterilization device to, for example, an operating field. Transfer devices can provide radiation protection during transfer of a seed holder from one area to another. In addition, a transfer device/seed holder assembly can be designed to mate with an applicator such that the transfer device protects the practitioner from radiation exposure while using the applicator together with a needle to implant radioactive seeds into a patient. Brachytherapy components such as the radioactive seeds, seed holders, and transfer devices are disclosed in U.S. patent application Ser. No. 09/792,307.

Staging-Sterilization Devices

The invention provides staging-sterilization devices that can be used as (1) containers for storing, transporting, and sterilizing radioactive seeds and (2) staging platforms for extracting radioactive seeds from or loading radioactive seeds into a seed holder. The diagrams provided herein depict different designs within the scope of the invention that incorporate components for sterilization and staging. Other designs incorporating these components are also within the scope of the invention.

Figure 1:
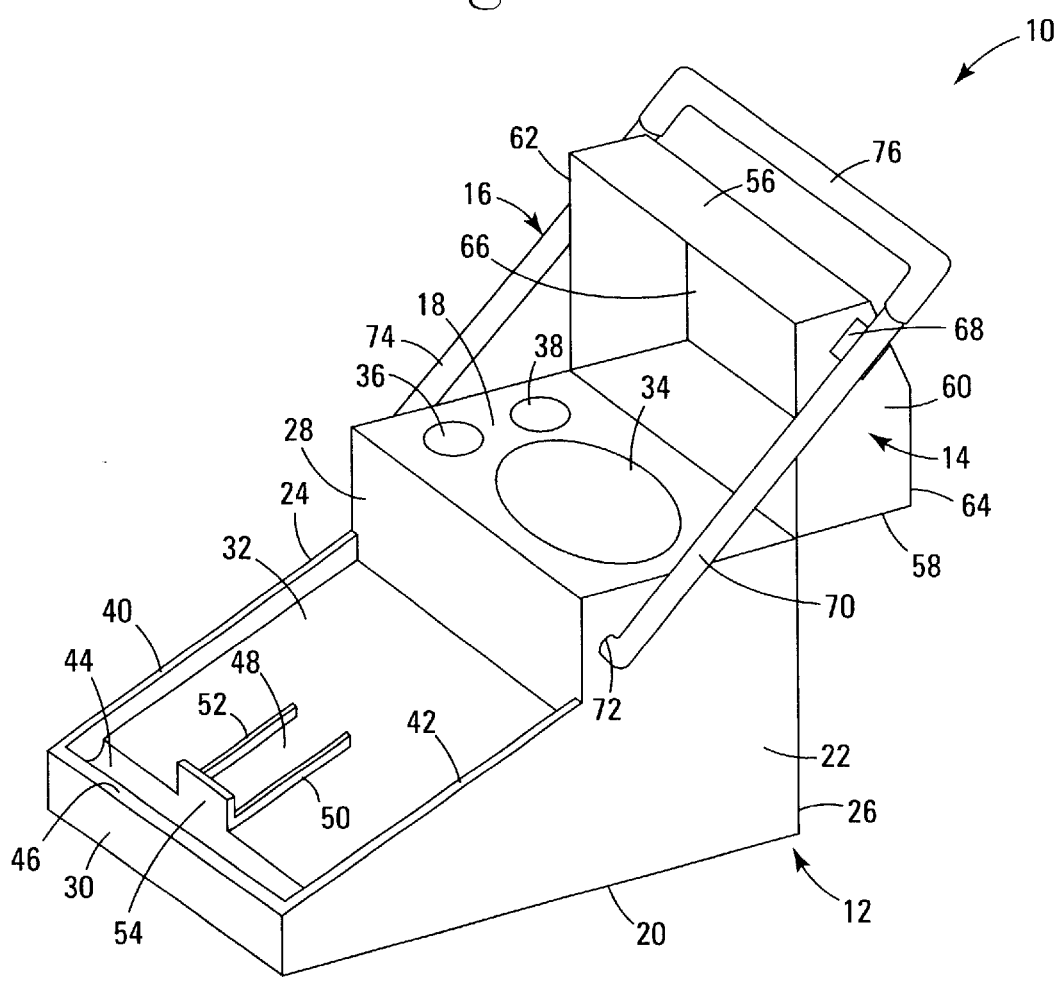
FIG. 1 is a diagram of a staging-sterilization device with the lid in an open position.

FIG. 1 is a diagram of staging-sterilization device in accordance with an embodiment of the present invention. As shown in FIG. 1, staging-sterilization device 10 can have body 12, lid 14, and handle 16. Body 12 can define body top surface 18, body bottom surface 20, body side 22, body side 24, body back 26, body front 28, body front 30, and staging area surface 32. Body bottom surface 20 can be designed to sit flat on a level surface such as a table. Body side 22, body side 24, body back 26, body front 28, and body front 30 can be perpendicular with respect to body bottom surface 20, while staging area surface 32 can be sloped toward body bottom surface 20. For example, staging area surface 32 can be at an angle less than 90 degrees (e.g., 80, 75, 60, 55, 50, 45, 40, 30, 20, or fewer degrees) with respect to body bottom surface 20. As a result of the slope of staging area surface 32, body front 28 and body front 30 can have a combined perpendicular height that is shorter than the height of body back 26.

Body top surface 18 can be an area that will be covered when lid 14 is in the closed position. Body top surface 18 can define insert receiving well 34. Insert receiving well 34 can be any shape capable of receiving an insert device. Such shapes include, without limitation, circular, oval, rectangular, and square shapes. In addition, insert receiving well 34 can have a depth capable of receiving the majority of an insert device while allowing a practitioner to grasp the insert with tweezers or fingers. Further, the depth of insert receiving well 34 can be such that when lid 14 is closed, the space between the bottom of insert receiving well 34 and the interior top surface of lid 14 is just enough to retain an insert device securely and prevent the insert device from moving up or down if the staging-sterilization device is tipped or inverted. Body top surface 18 can define one or more than one insert receiving well (e.g., two, three, four, five, or more insert receiving wells).

Body top surface 18 also can define transfer device well 36 and transfer device well 38. Transfer device wells 36 and 38 can be any shape capable of receiving a transfer device. Such shapes include, without limitation, circular, oval, rectangular, and square shapes. In addition, transfer device wells 36 and 38 can have a depth capable of receiving the majority of a transfer device while allowing a practitioner to grasp the transfer device with tweezers or fingers. Further, the depth of transfer device wells 36 and 38 can be such that when lid 14 is closed, the space between the bottom of the transfer device wells and the interior top surface of lid 14 is just enough to retain a transfer device securely and prevent the transfer device from moving up or down if the staging-sterilization device is tipped or inverted. Body top surface 18 can define one or more than one transfer device well (e.g., two, three, four, five, or more transfer device wells).

Staging area surface 32 can be bordered by lip 40 and lip 42. Lips 40 and 42 can be configured to prevent radioactive seeds from rolling over body side 22 or body side 24. The lower edge of staging area surface 32 can define trough 44 and lip 46. Trough 44 and lip 46 can be configured such that radioactive seeds dropped over staging area surface 32 are collected in trough 44 as opposed to rolling over lip 46 and body front 30. The bottom of trough 44 can be curved and positioned such that radioactive seeds collecting in trough 44 are easily observable by a practitioner. Likewise, the bottom of trough 44 can be curved and positioned to allow a practitioner to pick-up radioactive seeds easily and quickly with tweezers. These features can ensure that dropped radioactive seeds are not hidden from view, hung up in the staging-sterilization device, or lost altogether.

Staging area surface 32 also can include loading area 48, which is at least partially surrounded by seed holder supports 50, 52, and 54. Seed holder supports 50, 52, and 54 can be designed to hold a seed holder securely in place during the loading process. Loading area 48 of staging area surface 32 can be used to remove seeds from or insert seeds into a seed holder, for example, during assaying of the radioactive seeds before sterilization. The angle of staging area surface 32 with respect to body bottom surface 20 can be designed such that a seed holder secured in loading area 48 is easily visible to a practitioner when staging-sterilization device 10 is placed behind a leaded glass radiation shield. To facilitate visualization, staging area surface 32 can be at an angle of about 50 degrees relative to body bottom surface 20.

Lid 14 can have lid front 56, lid back 58, lid side 60, lid side 62, and lid top 64. In addition, lid front 56, lid back 58, lid sides 60 and 62, and lid top 64 can define inner lid region 66. Lid sides 60 and 62 each can provide a surface for attaching a handle guide. For example, handle guide 68 can be attached to or integral to lid side 60. Likewise, another handle guide can be attached to lid side 62. Handle guides can be configured such that the opening and closing of lid 14 can be actuated by movement of handle 16. As a result, a practitioner can open or close lid 14 with one hand and without coming into direct contact with lid 14, thus minimizing radiation exposure. In addition, a portion of lid top 64 can be sloped downward toward lid front 56 to provide a comfortable finger clearance (e.g., ¾ inch) when a practitioner is holding onto handle 16, especially when lid 14 is in the open position.

Each arm of handle 16 can be attached to a body side. For example, handle arm 70 can be attached to handle attachment site 72 of body side 22. Likewise, handle arm 74 can be attached to a handle attachment site of body side 24. The top portion of handle 16 can incorporate thermal barrier 76 to provide safer handling of staging-sterilization device 10 after sterilization. Suitable materials for thermal barrier 76 include, for example, silicone or polyvinyl chloride tubing.

Figure 2:
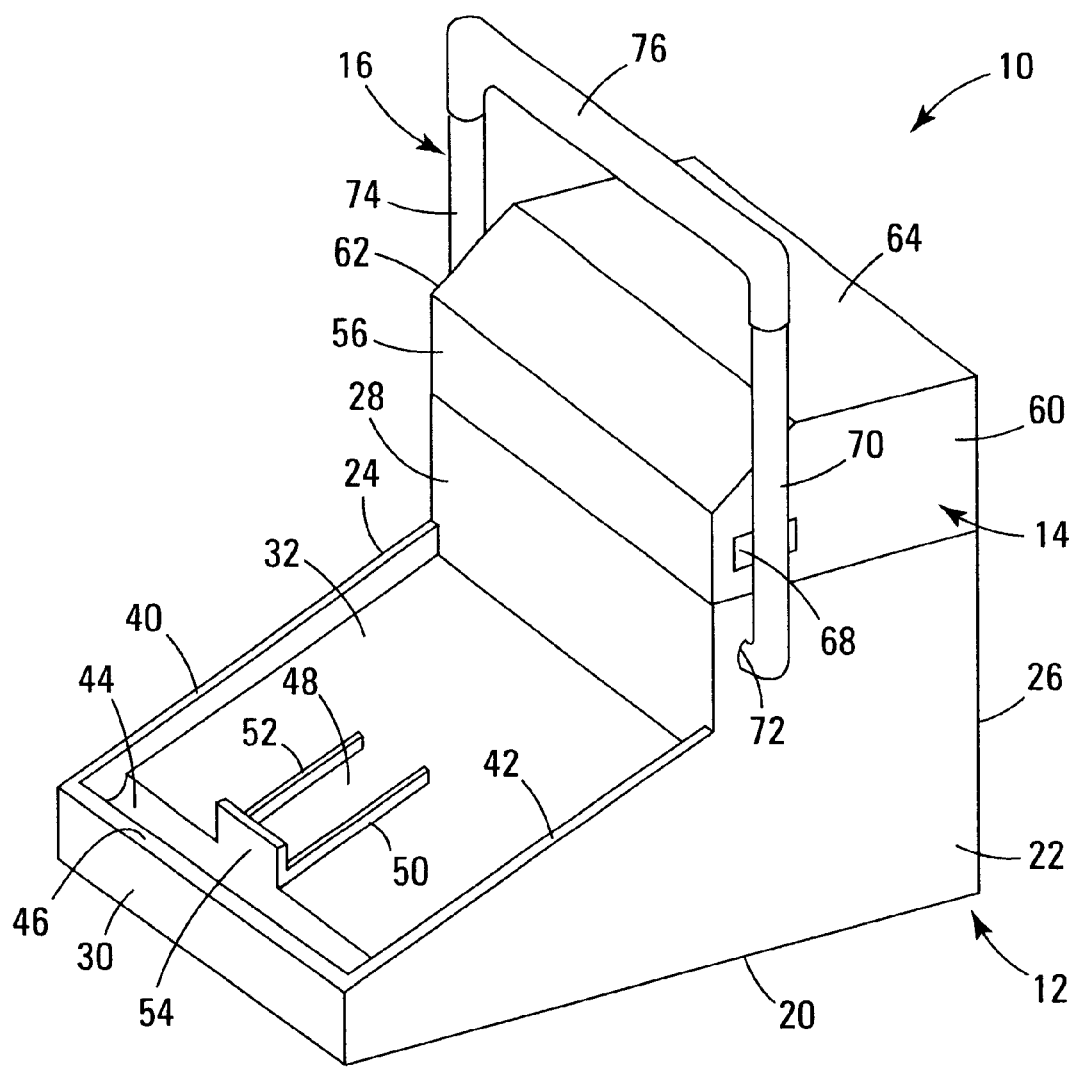
FIG. 2 is a diagram of the staging-sterilization device from FIG. 1 with the lid in a closed position.

Lid 14, handle 16, the handle attachment sites, and handle guides can be configured such that pushing pressure (pressure applied from the front toward the back) applied against thermal barrier 76 causes handle 16 to move from a vertical position to the angled position shown in FIG. 1, thus opening lid 14. In addition, the configuration can be such that pulling pressure (pressure applied from the back toward the front) applied against thermal barrier 76 causes handle 16 to move from the angled position shown in FIG. 1 to a more vertical position, thus closing lid 14. FIG. 2 is a diagram of staging-sterilization device 10 from FIG. 1 with lid 14 in the closed position.

Any material can be used to make body 12, lid 14, and handle 16. For example, stainless steel, aluminum (e.g., anodized aluminum), or titanium can be used to make body 12, lid 14, and handle 16. In addition, such materials can be used in combination with a high radiation shielding material such as lead or tungsten. For example, body 12, lid 14, and handle 16 can be made from aluminum having a lead lining. Typically, body 12 and lid 14 are made from a material that can (1) provide radiation protection and (2) transfer heat quickly. In one embodiment, anodized aluminum is used to make body 12 and lid 14, while stainless steal is used to make handle 16. In addition, body 12, lid 14, and handle 16 can be, individually, machined from a solid piece of metal (e.g., aluminum) or can be, individually, formed from multiple metal pieces held together with, for example, welded joints. Typically, body 12 and lid 14 are, individually, machined from a solid piece of aluminum to reduce the possibility of radiation leakage through welded joints. Body 12 and lid 14 can have any thickness sufficient to provide an adequate level of radiation protection. For example, lid 14 can be ¼-, ½-, ¾-, or 1-inch thick.

Figure 3:
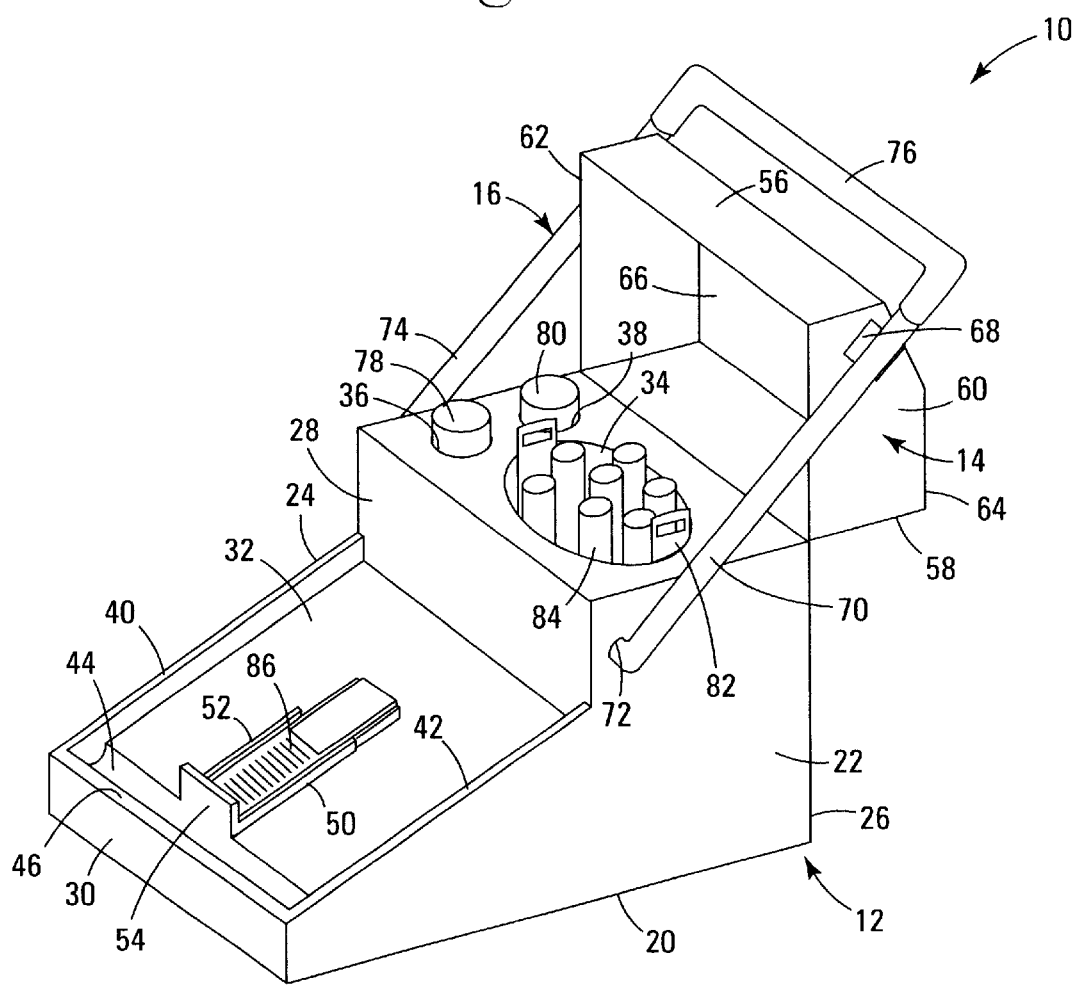
FIG. 3 is a diagram of the staging-sterilization device from FIG. 1 with the lid in an open position and with the staging-sterilization device containing additional brachytherapy components.

FIG. 3 is a diagram of staging-sterilization device 10 from FIG. 1 containing additional brachytherapy components. As shown in FIG. 3, transfer device wells 36 and 38 can be configured to hold transfer devices 78 and 80, respectively. In addition, insert receiving well 34 can be configured to hold insert device 82. Insert device 82, as shown in FIG. 3, contains seven seed holders, one of which is labeled seed holder 84. Another seed holder, seed holder 86, is shown positioned in loading area 48. While positioned in loading area 48, seed holder 86 can be loaded with radioactive seeds.

Figure 4:
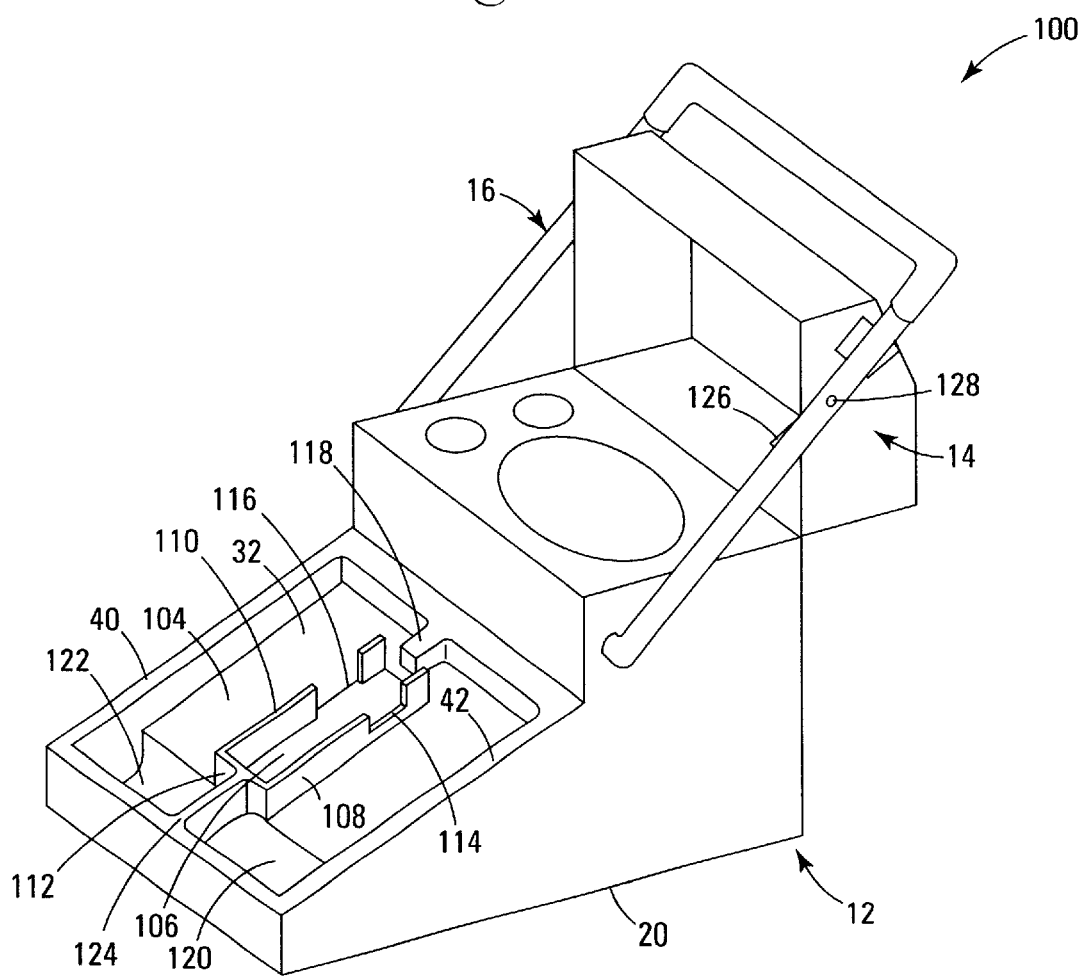
FIG. 4 is a diagram of a staging-sterilization device with the lid in an open position.

FIG. 4 is a diagram of staging-sterilization device 100 in accordance with another embodiment of the present invention. As shown in FIG. 4, staging area 32 of staging-sterilization device 100 can be separated into portion 102 and portion 104 by raised loading area 106. Raised loading area 106 can be at least partially surrounded by seed holder supports 108, 110, and 112. Seed holder supports 108 and 110 can contain openings 114 and 116, respectively. Openings 114 and 116 can allow the practitioner to grip a seed holder positioned in raised loading area 106. The area of staging area 32 above raised loading area 106 can contain upper extension 118. Upper extension 118 can be configured to restrict movement of a seed holder positioned in loading area 106. The lower edge of staging area surface 32 can define troughs 120 and 122 separated by lower extension 124. Trough 120 and lip 42 can be configured such that radioactive seeds dropped over portion 102 of staging area surface 32 are collected in trough 120, while trough 122 and lip 40 can be configured such that radioactive seeds dropped over portion 104 of staging area surface 32 are collected in trough 122.

Figure 5:
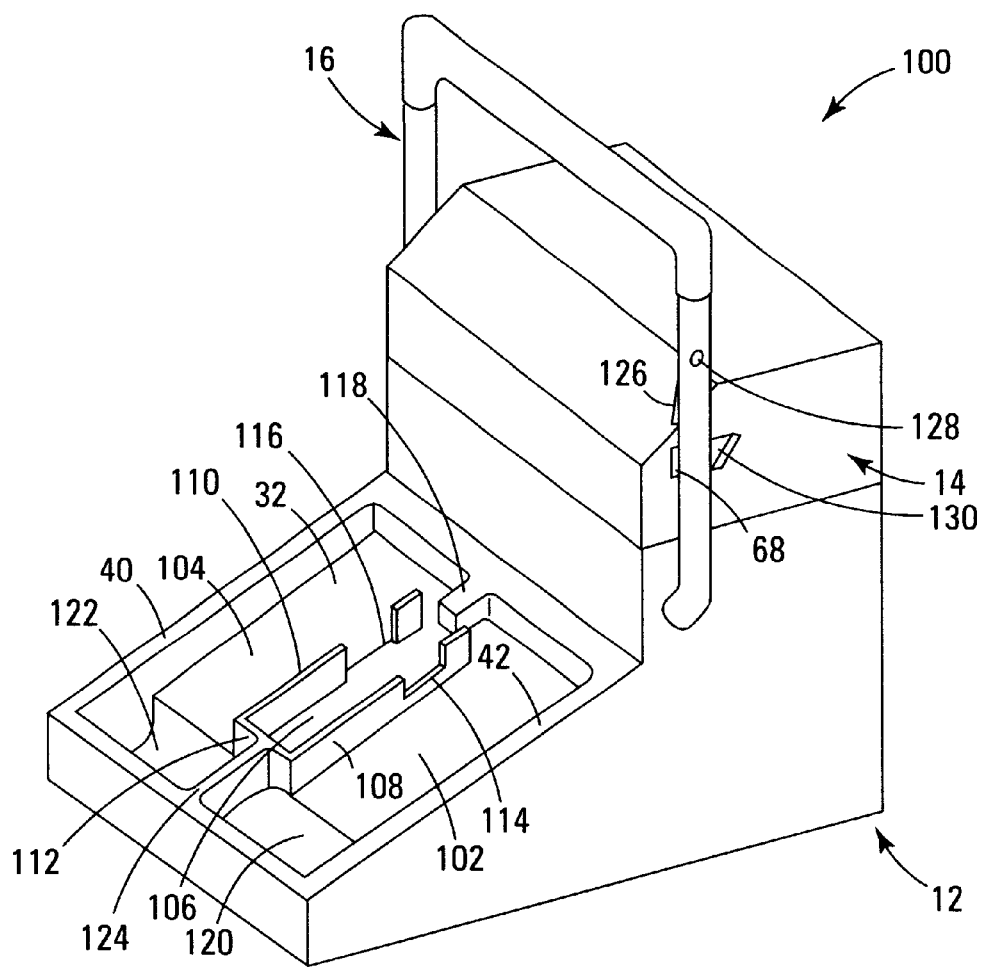
FIG. 5 is a diagram of the staging-sterilization device from FIG. 4 with the lid in a closed position.

As shown in FIG. 4, handle 16 of a staging-sterilization device can have an integral locking mechanism that incorporates locking lever 126 and recessed actuation button 128. Locking lever 126 can be configured to fit securely over lid 14 when lid 14 is in a closed position, thus holding lid 14 firmly closed and keeping lid 14 closed even if the staging-sterilization device is completely inverted. FIG. 5 is a diagram of staging-sterilization device 100 from FIG. 4 with lid 14 in the closed position. Recessed actuation button 128 can be configured such that depression of recessed actuation button 128 causes locking lever 126 to retract into handle 16, thus allowing lid 14 to be opened. One or both arms of a handle can contain an integral locking mechanism. As shown in FIG. 5, handle guide 68 can have face 130 to provide an opening stop for handle 16 and to minimize stress on handle guide 68.

Figure 6:
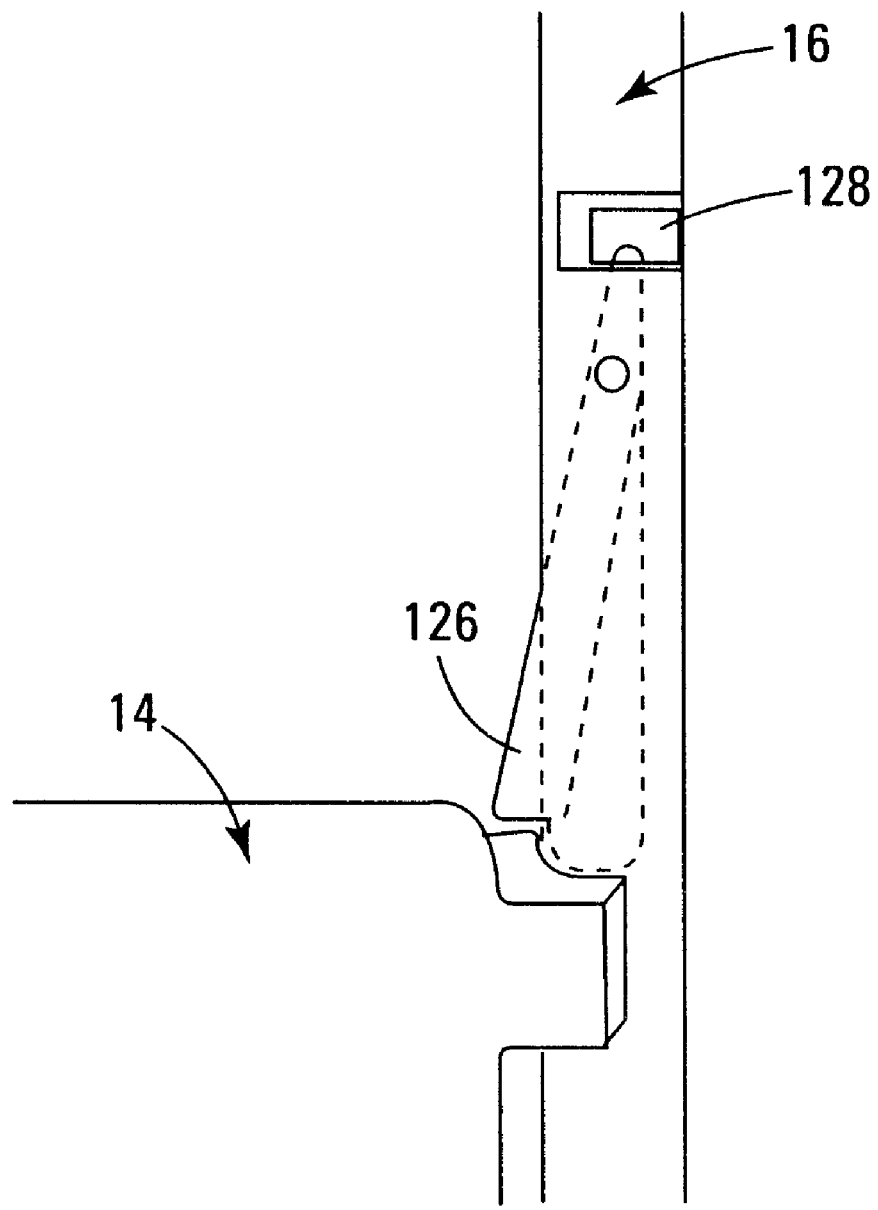
FIG. 6 is a close-up cross-sectional diagram of a locking mechanism in a handle from a staging-sterilization device.

FIG. 6 is a close-up, cross-sectional view of one embodiment of a locking mechanism in handle 16. As shown in FIG. 6, locking lever 126 can prevent lid 14 from being opened. In addition, recessed actuation button 128 can be recessed such that the locking mechanism is not accidentally actuated. Again, when recessed actuation button 128 is depressed, locking lever 126 retracts into handle 16, allowing lid 14 to be opened. Recessed actuation button 128 can be spring-loaded such that locking lever 126 is in the extended position shown in FIG. 6 unless a practitioner presses recessed actuation button 128. This locking mechanism can be designed to be easily operated with one hand, reducing radiation exposure. In addition, recessed actuation button 128 can have a spherical diameter equal to the cylindrical diameter of handle 16, to create a surface finish pattern that is easy to find visually on handle 16. Handle 16 can be mounted such that recessed actuation button 128 can be operated with either the right or left hand.

Figure 7:
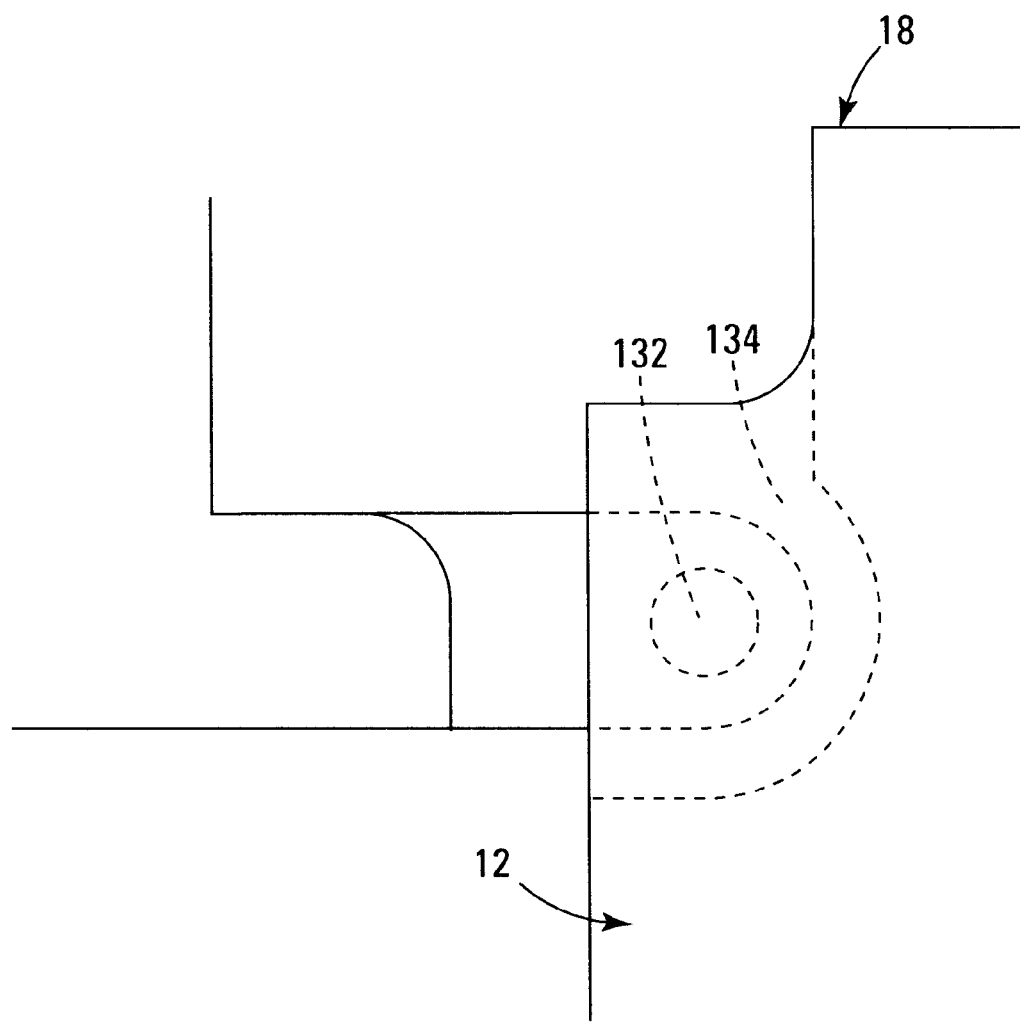
FIG. 7 is a close-up diagram of an integral hinge of a staging-sterilization device.

As shown in FIGS. 1 and 4, lid 14 can be attached to body 12. Typically, lid 14 is attached to body 12 by one or more hinges such that when lid 14 is in the closed position lid 14 covers body top surface 18 as shown in FIGS. 2 and 5. FIG. 7 is a close-up view of integral hinge 132. As shown in FIG. 7, lid 14 can be attached to body 12 by integral hinge 132 that is integral to lid 14. Body back 26 of body 12 can define cutout 134 for integral hinge 132. In addition, cutout 134 can have fillets to prevent entrapment of radioactive seeds that have accidentally dislodged and can have large radius clearance such that radioactive seeds will roll out underneath hinge 132.

Figure 8:
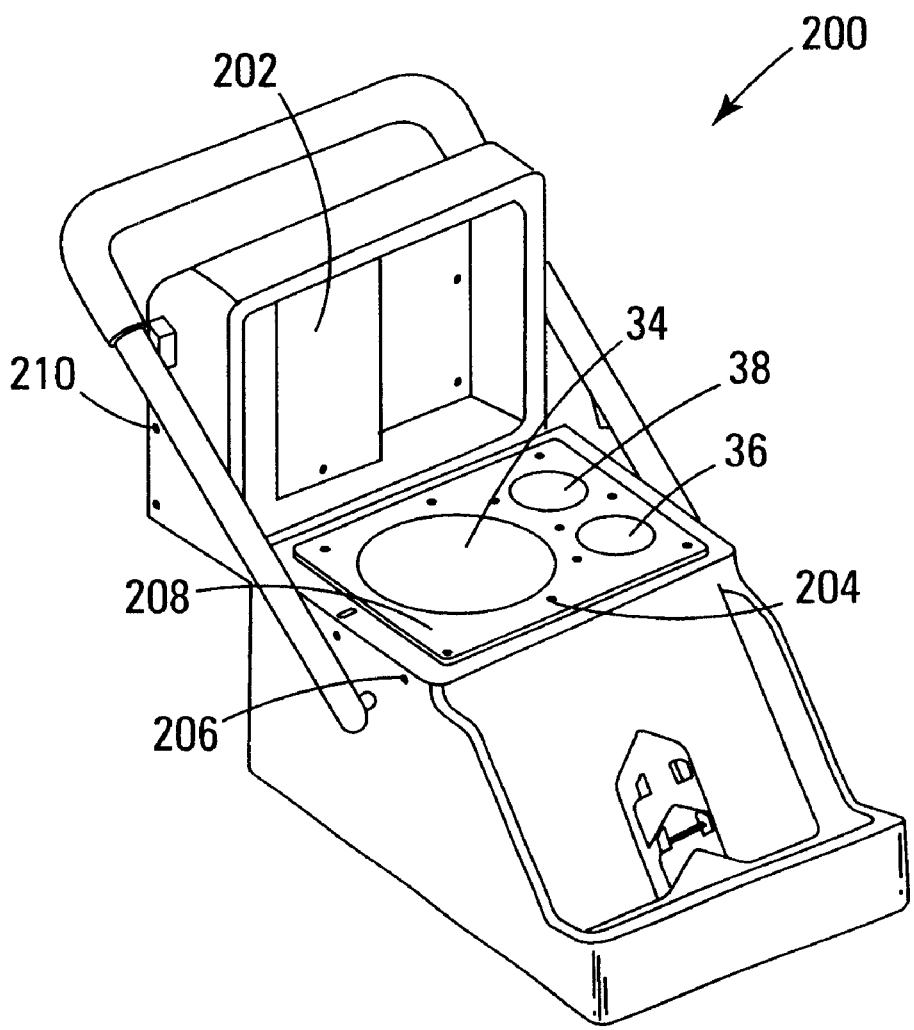
FIG. 8 is a diagram of a staging-sterilization device with the lid in an open position.

FIG. 8 is a diagram of staging-sterilization device 200 in accordance with another embodiment of the present invention. As shown in FIG. 8, body 12 can be configured to have multiple body vents, one of which is labeled 204. Likewise, lid 14 can be configured to have multiple lid vents, one of which is labeled 210. Body vents and lid vents can facilitate heating and cooling of the staging-sterilization device during and after sterilization. In addition, body vents and lid vents can provide a means by which condensation (formed as a result of sterilization) can escape from the staging-sterilization device. Body vents and lid vents can be positioned and dimensioned (e.g., with a diameter of approximately ⅛ inch) such that there is no direct line of sight to any radioactive seeds when the staging-sterilization device contains radioactive seeds. In addition, body vents can be at any angle relative to body bottom surface 20. Lid vents can be at any angle relative to lid top 64. For example, as shown in FIG. 8, staging-sterilization device 200 can have horizontal body vents (one of which is labeled 206) and vertical body vents (one of which is labeled 204). Body vents and lid vents can penetrate straight through the staging-sterilization device creating a line of sight through the staging-sterilization device or can be designed to penetrate the staging-sterilization device in an internally connected manner such that a line of sight is not created through the staging-sterilization device. For example, a vertical body vent can be internally connected to a horizontal body vent.

As shown in FIG. 8, lid 14 can have an interior surface defining protrusion 202. Protrusion 202 can be designed such that protrusion 202 is positioned directly above seed holders contained within an insert device positioned within insert receiving well 34 when lid 14 is in a closed position but not above the pick-up handles of an insert device positioned within insert receiving well 34 when lid 14 is in a closed position. In other words, protrusion 202 can be designed to fit between the pick-up handles on an insert device when insert receiving well 34 contains an insert device and when lid 14 is in a closed position. In addition, protrusion 202 can be configured to provide an appropriate clearance (e.g., 0.05 inches) between the surface of protrusion 202 and the top of seed holders contained within an insert device that is positioned within insert receiving well 34 when lid 14 is in a closed position. In such a configuration, protrusion 202 can securely retain an insert device and any seed holders contained within the insert device. For example, when lid 14 is securely closed and locked, staging-sterilization device 200 can be carried or placed in any position, without concern that seed holders or radioactive seeds will become disengaged or displaced. Positioning a protrusion such that it secures any seed holders within an insert device placed in an insert receiving well can prevent both the insert device and the seed holders from moving should the staging-sterilization device be tipped or inverted, ensuring that radioactive seeds are firmly retained within seed holders. Further, protrusion 202 can provide increased protection from radiation by providing shielding above radioactive seeds contained within seed holders secured in an insert device positioned within an insert receiving well. Likewise, the section of lid 14 directly above transfer device wells 36 and 38 can have a thickness such that when lid 14 is closed, transfer devices within transfer device wells 36 and 38 are securely retained.

As shown in FIG. 8, body top surface 18 can define protruding deck 208. Protruding deck 208 can provide additional radiation protection by fitting within lid 14, thus removing a line of sight to a radioactive seed when lid 14 is in a closed position.

Figure 9:
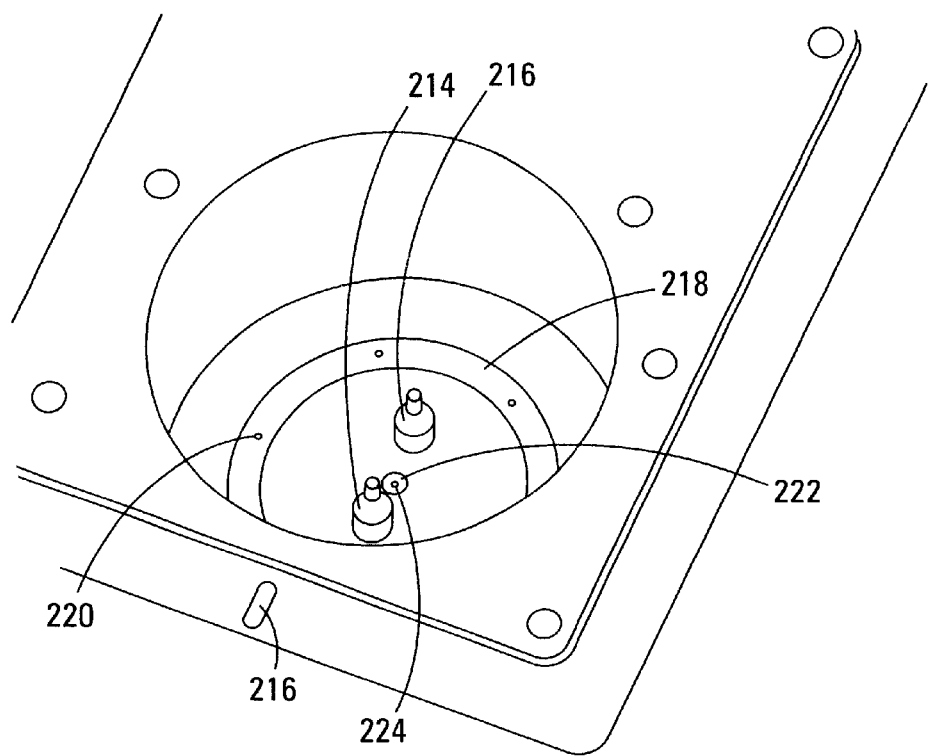
FIG. 9 is a overhead diagram of the insert receiving well of the staging-sterilization device from FIG. 8.

FIG. 9 is an overhead diagram of insert receiving well 34 of staging-sterilization device 200 from FIG. 8. As shown in FIG. 9, insert receiving well 34 can contain pins 212 and 214 adapted to engage the bottom of an insert device. Pins 212 and 214 can be used to facilitate the correct positioning of an insert device within insert receiving well 34 such that protrusion 202 fits over any seed holders contained within an insert device as described herein. In addition, pins 212 and 214 can be conical in shape such that gravity aligns an insert device that is inadvertently misaligned by less than about 45 degrees. The angle of the conical shape (e.g., 20 degrees) and the location of the pins close to the bottom of insert receiving well 34 can provide a cushioned landing for an inadvertently misaligned insert device by converting translational energy into rotational energy. Further, body top surface 18 can contain alignment indicator 216 to assist a practitioner with correctly positioning an insert device within insert receiving well 34.

Also as shown in FIG. 9, insert receiving well 34 can contain groove 218 having vents (one of which is labeled 220). Groove 218 can be used to provide a fluid connection between different vents. Insert receiving well 34 also can contain recess 222 having vent 224. The vents within insert receiving well 34 can be similar to the body vents and lid vents described herein. Alternatively, the vents within insert receiving well 34 can be smaller than the body vents and lid vents described herein. For example, the vents within insert receiving well 34 can have a diameter of 0.028 inch or less. Such smaller vents can be used to prevent loose radioactive seeds from entering the vents.

The bottom surface of insert receiving well 34 can have a chamfer to provide a better angular hold on an insert device that is positioned within insert receiving well 34.

The transfer device wells of a staging-sterilization device can contain vents similar to the body vents, lid vents, or the vents within an insert receiving well described herein.

Figure 10:
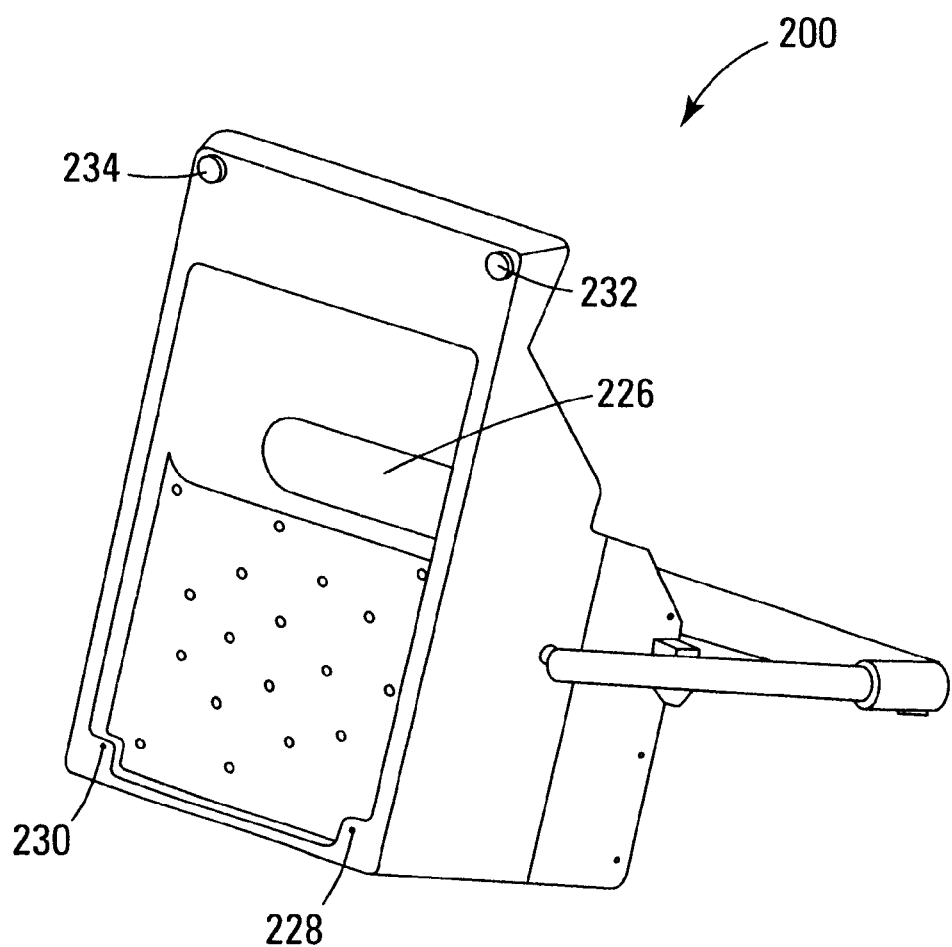
FIG. 10 is a diagram of the bottom of the staging-sterilization device from FIG. 8.

FIG. 10 is a diagram of the bottom surface of staging-sterilization device 200 from FIG. 8. As shown in FIG. 10, body 12 can have a hollow bottom 226. Hollow bottom 226 can be positioned underneath staging area surface 32 such that radiation shielding is not compromised. Hollow bottom 226 can provide reduced heat capacity, reducing the time needed to heat and cool staging-sterilization device 200. Further, hollow bottom 226 can make staging-sterilization device 200 lighter and easier to carry, and can shift the center of gravity toward the back of staging-sterilization device 200 to promote gravity closure of lid 14 when staging-sterilization device 200 is picked up or carried by handle 16. In addition, as shown in FIG. 10, the four corners of body bottom surface 20 can have holes (two of which are labeled 228 and 230) adapted to receive mounting feet (two of which are labeled 232 and 234). Such holes and mounting feet can be positioned at any location on the body bottom surface.

Figure 11:
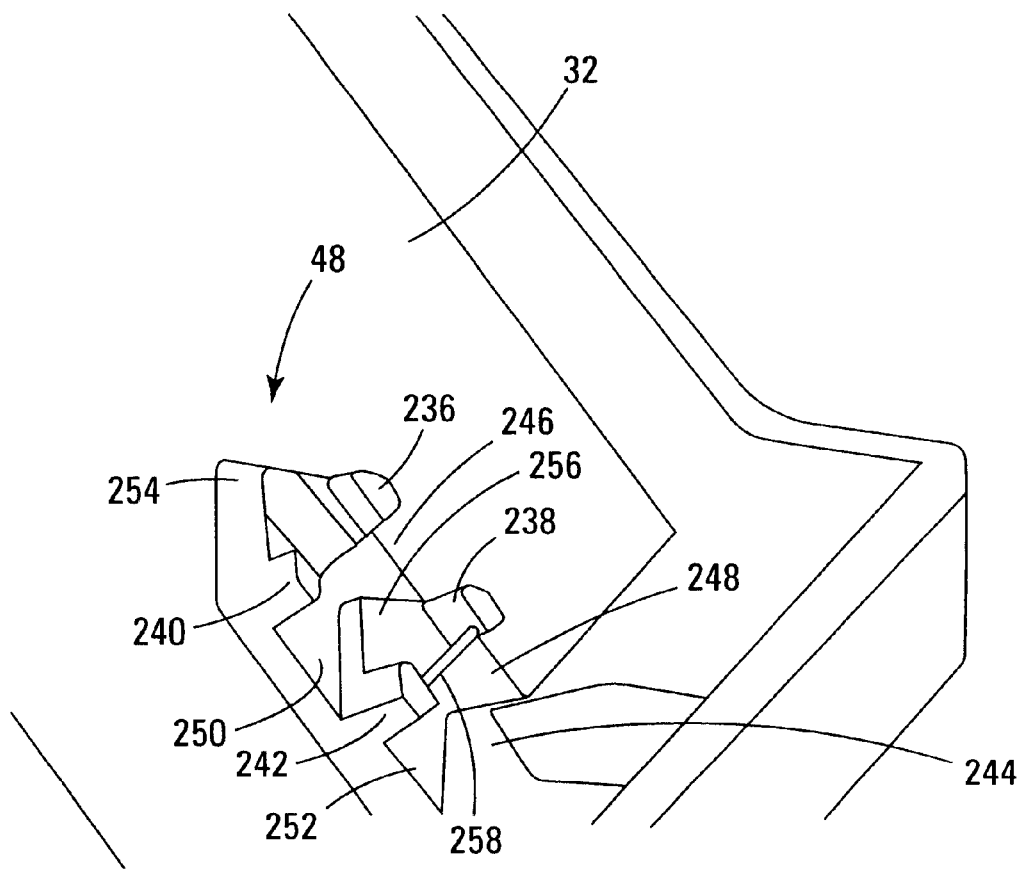
FIG. 11 is a close-up diagram of the loading area of the staging-sterilization device from FIG. 8.

FIG. 11 is a close-up diagram of the loading area of staging-sterilization device 200 from FIG. 8. As shown in FIG. 11, loading area 48 can be raised above staging area surface 32. In addition, loading area 48 can be at least partially bordered by seed holder supports 236, 238, 240, and 242 and bottom seed holder support 244. Seed holder supports 236, 238, 240, and 242 can be spaced apart such that a radioactive seed can pass freely through (1) opening 246 located between seed holders 236 and 238, (2) opening 248 located between seed holder 238 and bottom seed holder 244, (3) opening 250 located between seed holders 240 and 242, and (4) opening 252 located between seed holder 242 and bottom seed holder 244. In addition, seed holder supports 236, 238, 240, and 242 and bottom seed holder support 244 can be designed to match the shape of a seed holder, thus preventing lateral movement of the seed holder once positioned in loading area 48.

Loading area 48, as shown in FIG. 11, can have top portion 254 and inner portion 256. Top portion 254, inner portion 256, and bottom seed holder support 244 can be pointed, angled, or pointed and angled to facilitate a downward motion of accidentally dropped radioactive seeds. In addition, loading area 48 can have restraining wire 258 extending from seed holder support 238 to seed holder support 242. Restraining wire 258 can be configured to hold a seed holder firmly in place once positioned in loading area 48, thus preventing axial movement of the seed holder. The loading area of a staging-sterilization device can have one or more than one restraining wire. For example, a staging-sterilization device can have two, three, four, or more restraining wires. Each restraining wire of a staging-sterilization device can positioned such that the view to any radioactive seeds within a positioned seed holder is not blocked. Alternatively, a movable lever can be used to hold a seed holder firmly in place. For example, a movable lever can be used to restrict all movements of a seed holder placed within the loading area.

Figure 12:
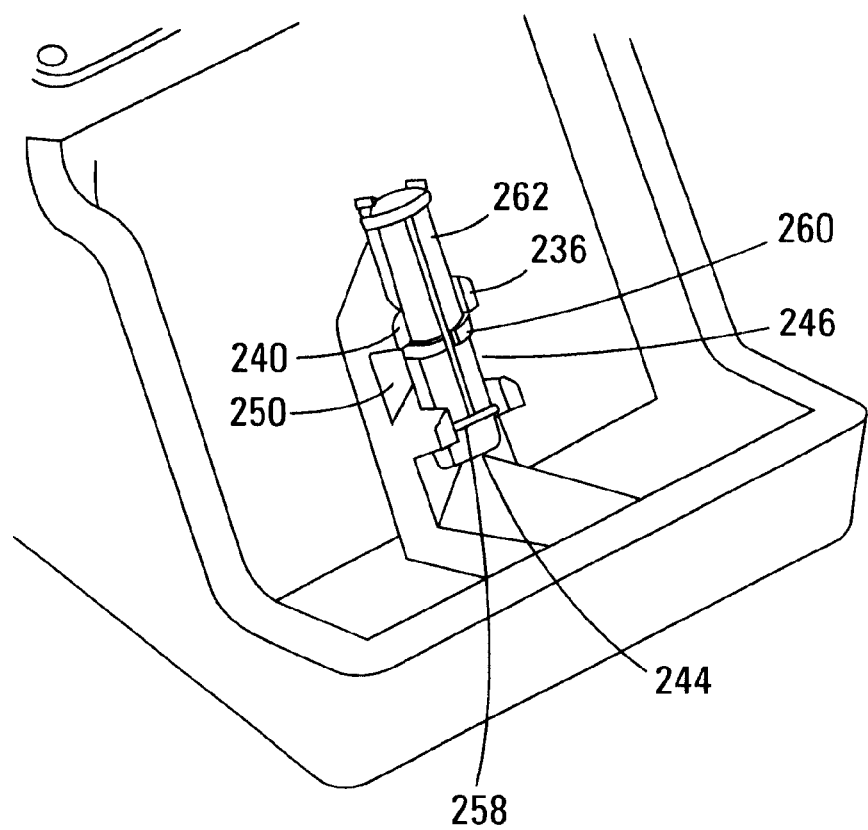
FIG. 12 is a close-up diagram of a seed holder positioned in the loading area of the staging-sterilization device from FIG. 8.
Figure 13:
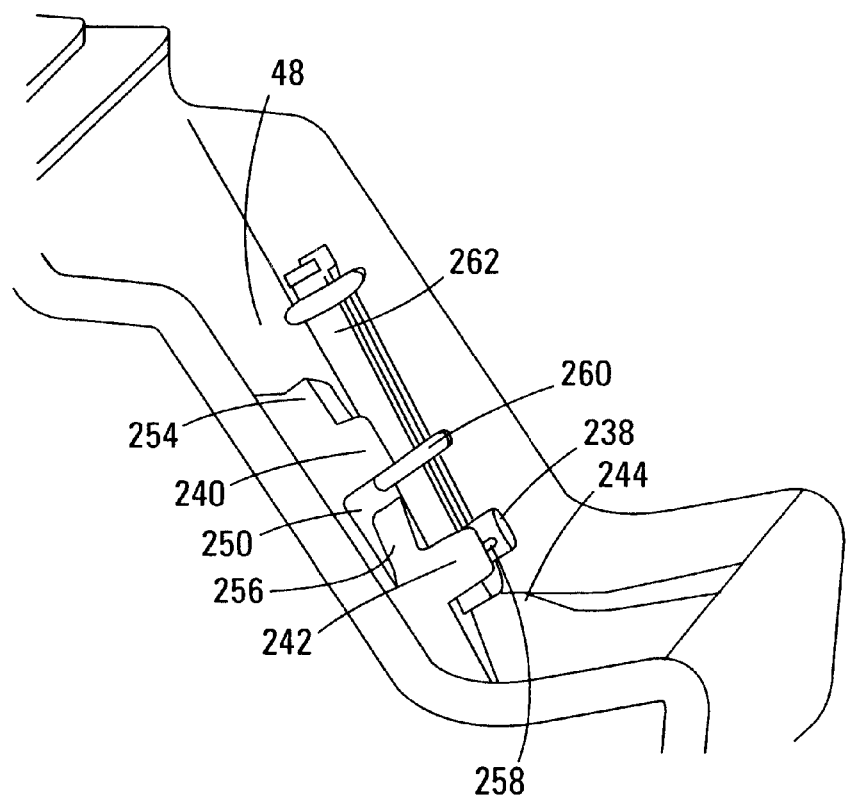
FIG. 13 is a close-up side-view diagram of a seed holder positioned in the loading area of the staging-sterilization device from FIG. 8.

FIG. 12 is a diagram of a seed holder positioned in the loading area of staging-sterilization device 200 from FIG. 8. FIG. 13 is a side-view diagram of a seed holder positioned in the loading area of staging-sterilization device 200 from FIG. 8. As shown in FIGS. 12 and 13, seed holder 262 can be positioned underneath restraining wire 258, thus preventing axial movement of seed holder 262. In addition, seed holder supports 236 and 240 as well as openings 246 and 250 can be designed such that ledge 260, which encircles seed holder 262, is positioned underneath seed holder supports 236 and 240 when seed holder 262 rests on top of bottom seed holder support 244. Such a design can prevent longitudinal movement of seed holder 262 once positioned in loading area 48.

Figure 14:
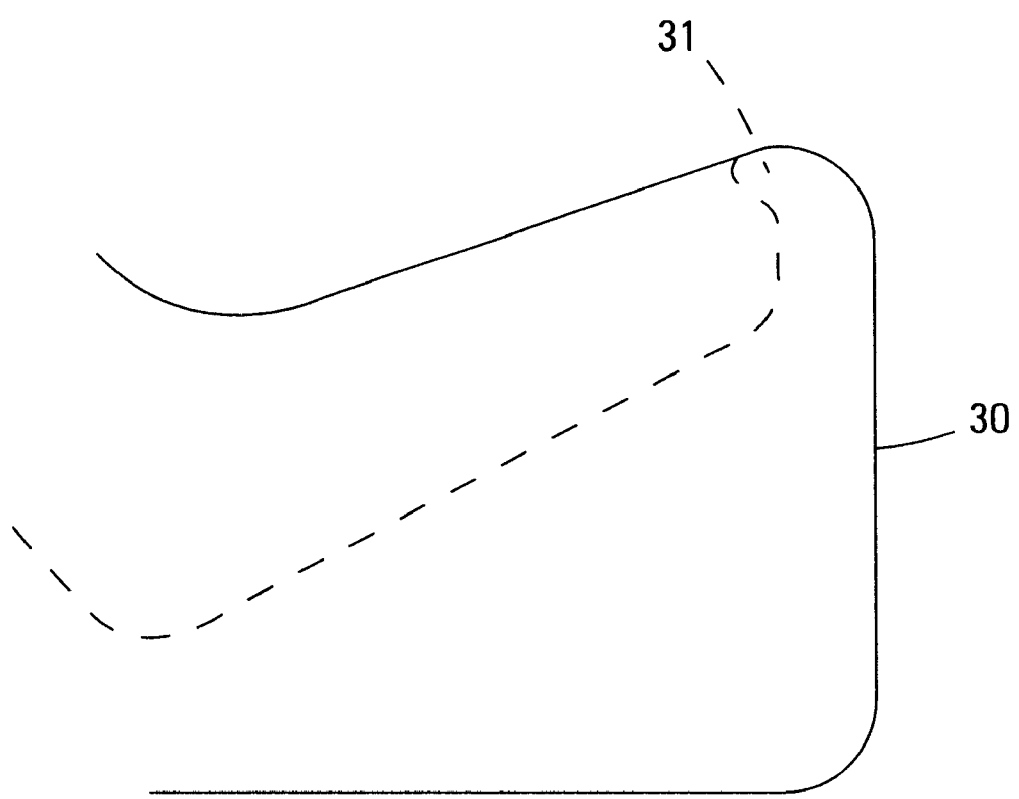
FIG. 14 is a close-up cross-sectional diagram of a trough of a staging-sterilization device.

As described herein with reference to FIG. 1, trough 44 and lip 46 can be configured such that radioactive seeds dropped over staging area surface 32 are collected in trough 44 as opposed to rolling over lip 46 and body front 30. As shown in FIG. 14, body front 30 can define overhang 31. Overhang 31 can be configured such that a rolling radioactive seed is directed toward the bottom of trough 44. In addition, the trough can define a surface configured such that collected radioactive seeds are both visible to a practitioner and directionally aligned. Such a directional alignment can allow the practitioner to pick-up each radioactive seeds without rotating the pick-up tool (e.g., tweezers) between pick-ups.

Insert Devices

The invention provides insert devices that can hold one or more seed holders (e.g., two, three, four, five, six, seven, eight, nine, ten, eleven, twelve, or more seed holders). The capacity of an insert device to hold multiple seed holders allows for efficient transfer of seed holders containing radioactive seeds, minimizing radiation exposure because there is no need to handle or move seed holders individually. The diagrams provided herein depict different designs within the scope of the invention that incorporate various insert device components. Other designs incorporating these components are also within the scope of the invention.

Figure 15:
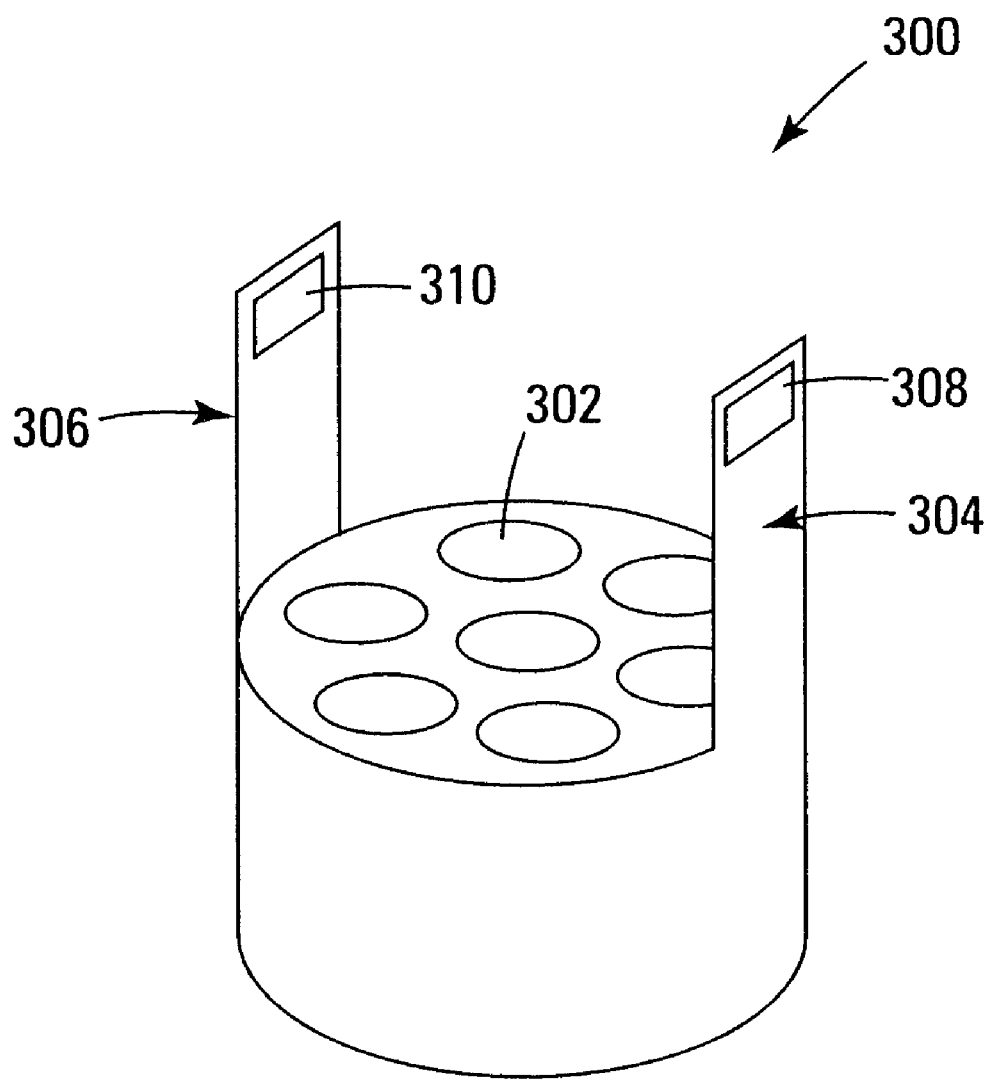
FIG. 15 is a diagram of an insert device.

FIG. 15 is a diagram of an insert device in accordance with an embodiment of the present invention. As shown in FIG. 15, insert device 300 can be configured to contain seven seed holder pockets, one of which is labeled 302. In addition, insert device 300 can have pick-up handles 304 and 306 to facilitate transfer of insert device 300, for example, from a shielded shipping container to a staging-sterilization device. Pick-up handles 304 and 306 can define apertures 308 and 310, respectively. Apertures 308 and 310 can provide a convenient means for moving insert device 300. For example, reverse action tweezers, a common instrument used by practitioners handling brachytherapy radioactive seeds, can be inserted through apertures 308 and 310 to easily lift insert device 300. In this case, the practitioner would not need to handle insert device 300 directly, thus reducing radiation exposure. Apertures can have any shape (e.g., circular, square, or rectangular) and size. In addition, apertures can be located anywhere along the pick-up handles. For example, as shown in FIG. 15, apertures 308 and 310 can be located near the top of pick-up handles 304 and 306.

An insert device can have any number of pick-up handles (e.g., one, two, three, four, or more pick-up handles). In addition, pick-up handles can have any shape. For example, a pick-up handle can be a cylindrical or rectangular shaped extension (e.g., a rod).

Each seed holder pocket of an insert device can be designed to match the shape of a seed holder such that the seed holder can be securely held within the seed holder pocket, minimizing the risk that radioactive seeds will become dislodged during shipping or handling of the insert device. For example, if a seed holder has an oval shape, then the seed holder pockets of an insert device can be oval in shape. Similarly, if a seed holder has a cylindrical shape, then the seed holder pockets of an insert device can be cylindrical in shape. In addition, insert device 300 can be configured to fit within an insert receiving well of a staging-sterilization device.

Insert devices can be constructed from suitable materials such as plastic (e.g., polycarbonate, polystyrene, or polypropylene) or plastic filled with a radiation shielding material such as tungsten or lead. Typically, insert devices are designed to use a minimal amount of material. Such designs can minimize the time required to heat and cool the insert device during and after sterilization. In addition, an insert device can have one or more than one vent (e.g., two, three, four, five, six, seven, eight, nine, ten, or more vents) similar to the vents described with respect to the staging-sterilization devices disclosed herein. For example, the vents of an insert device can have a diameter that is smaller than the diameter of a radioactive seed.

Figure 16:
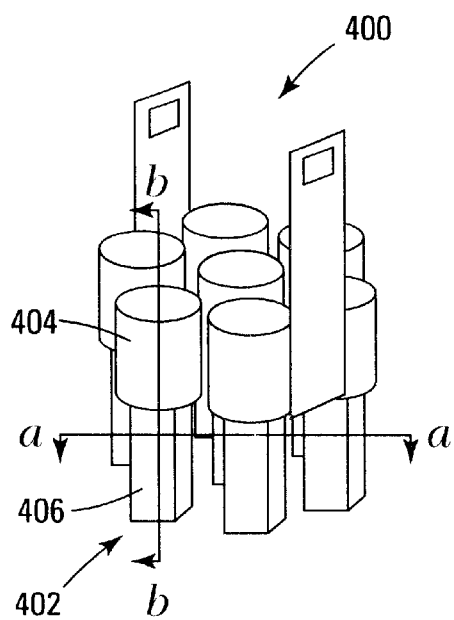
FIG. 16 is a diagram of an insert device.

FIG. 16 is a diagram of an insert device in accordance with an embodiment of the present invention. As shown in FIG. 16, insert device 400 contains seven seed holder pockets, one of which is labeled seed holder pocket 402. Each seed holder pocket can be irregularly shaped to match the irregular shape of a seed holder. For example, each seed holder pocket can be configured to have cylindrical top portion 404 and rectangular bottom portion 406 such that a seed holder having a rectangular shaped body with one or more circular ledges encircling the seed holder body fits securely within seed holder pocket 402.

Figure 17:
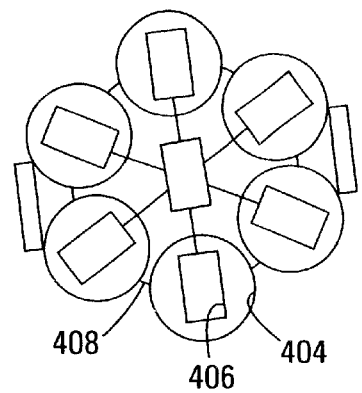
FIG. 17 is top view diagram of the insert device from FIG. 16.

FIG. 17 is top view diagram of the insert device from FIG. 16, depicting cylindrical top portion 404 and rectangular bottom portion 406. As shown in FIG. 17, seed holder pockets can be attached to one another via connectors, one of which is labeled connector 408. The connectors can be made as a single unit with the entire insert device. For example, the entire insert device can be made from plastic using a mold.

Figure 18:
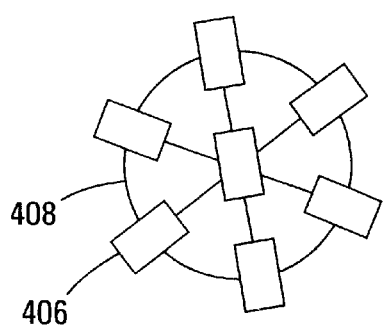
FIG. 18 is a diagram of the insert device from FIG. 16 from a transverse cross-sectional viewpoint taken along axis "a" of FIG. 16.

FIG. 18 is a diagram of the insert device from FIG. 16 from a transverse cross-section viewpoint taken along axis "a" of FIG. 16. As shown in FIG. 18, rectangular bottom portions of seed holder pockets can be attached to one another via connectors.

Figure 19:
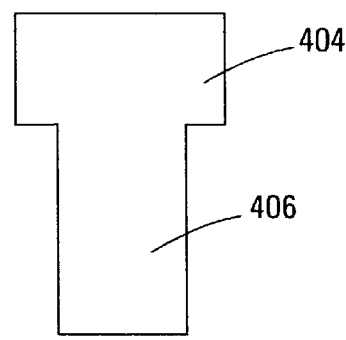
FIG. 19 is a diagram of the insert device from FIG. 16 from a longitudinal cross-sectional viewpoint taken along axis "b" of FIG. 16.

FIG. 19 is a diagram of the insert device from FIG. 16 from a longitudinal cross-sectional viewpoint taken along axis "b" of FIG. 16. As shown in FIG. 19, cylindrical top portion 404 is wider than rectangular bottom portion 406.

Figure 20:
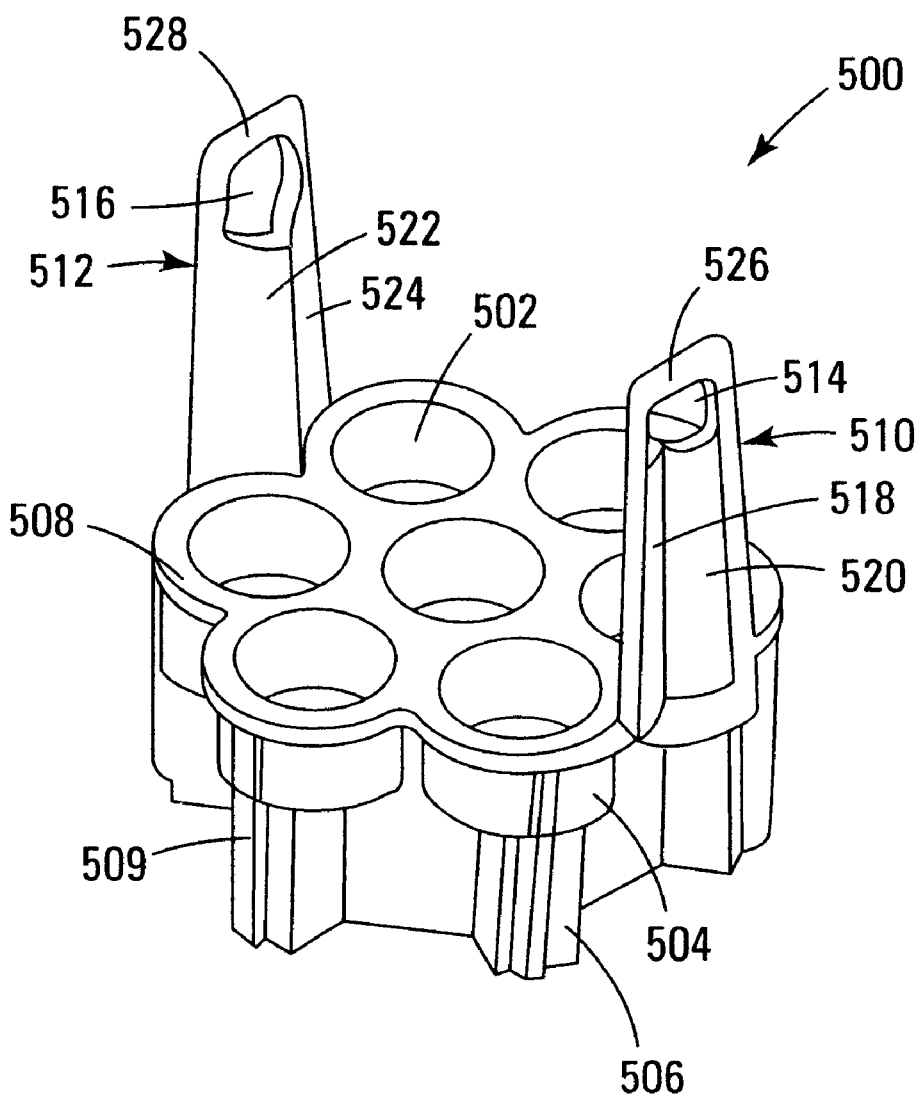
FIG. 20 is a diagram of an insert device.

FIG. 20 is a diagram of an insert device in accordance with another embodiment of the present invention. As shown in FIG. 20, insert device 500 can be configured to contain seven seed holder pockets, one of which is labeled seed holder pocket 502. Each seed holder pocket can be irregularly shaped to match the irregular shape of a seed holder. For example, each seed holder pocket can be configured to have cylindrical top portion 504 and rectangular bottom portion 506 such that a seed holder having a rectangular shaped body with one or more circular ledges encircling the seed holder body fits securely within seed holder pocket 502. Insert device 500 can have scalloped edge 508 surrounding the seed holder pockets. Scalloped edge 508 can reduce the amount of material required for insert device 500 and can facilitate installation of insert device 500 into an insert receiving well by reducing the likelihood of catching an edge of insert device 500 on the edge of the insert receiving well. Insert device 500 also can have vertical ledges (one of which is labeled vertical ledge 509) on the exterior of the seed holder pockets. Vertical ledges can provide stability and strength to an insert device.

As shown in FIG. 20, insert device 500 can have pick-up handles 510 and 512 defining apertures 514 and 516, respectively. Pick-up handles 510 and 512 can be configured to contain a geometrical contour that results in pick-up handle exterior surfaces 518 and 520 (shown on pick-up handle 510 of FIG. 20) and pick-up handle interior surfaces 522 and 524 (shown on pick-up handle 512 of FIG. 20). Such pick-up handle exterior and interior surfaces can facilitate finger pick-up of an insert device by a practitioner. In addition, pickup handles 510 and 512 can have vertical surfaces 526 and 528 above apertures 514 and 516, respectively. Vertical surfaces 526 and 528 can facilitate insertion of a pick-up tool (e.g., reverse action tweezers) into apertures 514 and 516 by a practitioner.

Figure 21:
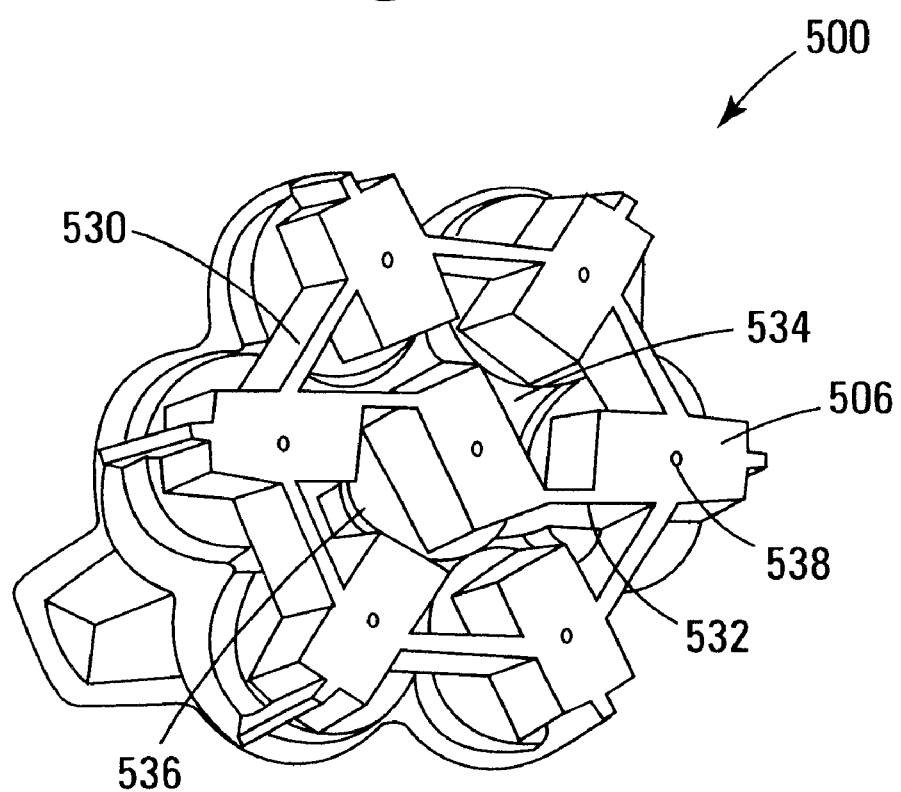
FIG. 21 is a diagram of the bottom of the inset device from FIG. 20.

FIG. 21 is a diagram of the bottom of insert device 500 shown in FIG. 20. As shown in FIG. 21, insert device 500 can have connectors (one of which is labeled connector 530) linking the bottom rectangular portions of the externally positioned seed holder pockets of insert device 500. Similarly, insert device can have connectors (one of which is labeled connector 532) linking the internally positioned seed holder pocket of insert device 500 to an externally positioned seed holder pocket of insert device 500. Such connectors can add strength and stability to an insert device, while keeping the amount of material required for construction of the insert device to a minimum. The connectors can be made as a single unit with the entire insert device. For example, the entire insert device can be made from plastic using a mold.

As shown in FIG. 21, insert device 500 can be configured such that the rectangular portions of the seed holder pockets are radially arranged. Such a configuration can minimize the time required to heat and cool an insert device and seed holders contained therein, by providing maximal space between each seed holder pocket. In addition, the configuration of the seed holder pockets and the connectors between the seed holder pockets can form spaces 534 and 536 on either side of an internally positioned seed holder pocket. Spaces 534 and 536 can be configured to engage pins located within an insert receiving well of a staging-sterilization device, thus serving to align and stabilize an insert device when inserted into the insert receiving well. Further, each seed holder pocket can have a vent, one of which is labeled vent 538. Vent 538 can be located at the bottom of a seed holder pocket such as in the center of rectangular bottom portion 506. Typically, the vents within an insert receiving well and within the seed holder pockets of an insert device will not be aligned when the insert device is positioned within the insert receiving well. In other words, the vents within an insert receiving well and within the seed holder pockets of an insert device can be positioned such that no line of sight is created through both the staging-sterilization device and the insert device when the insert device is positioned within the insert receiving well.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A brachytherapy device comprising:
  a) a body comprising a top surface, a bottom surface, and a staging area surface, wherein said top surface comprises an insert receiving well capable of holding an insert device, and wherein said staging area surface slopes away from said top surface and toward said bottom surface, and wherein said staging area surface comprises a loading area having one or more seed holder supports capable of holding a seed holder; and
  b) a lid attached to said body, wherein said lid is capable of opening to expose said insert receiving well and is capable of closing over said top surface to cover said insert receiving well.

2. The brachytherapy device of claim 1, wherein said body comprises a vent that creates a line of sight through said body.

3. The brachytherapy device of claim 2, wherein said vent extends from said top surface to said bottom surface.

4. The brachytherapy device of claim 1, wherein said body comprises a vent that does not create a line of sight through said body.

5. The brachytherapy device of claim 4, wherein said vent extends from said insert receiving well to said bottom surface.

6. The brachytherapy device of claim 1, wherein said top surface is substantially parallel with a flat surface when said bottom surface rests on said flat surface.

7. The brachytherapy device of claim 1, wherein said top surface comprises multiple insert receiving wells.

8. The brachytherapy device of claim 1, wherein said top surface comprises a transfer device well capable of holding a transfer device.

9. The brachytherapy device of claim 1, wherein said top surface comprises multiple transfer device wells.

10. The brachytherapy device of claim 1, wherein a portion of said top surface is raised.

11. The brachytherapy device of claim 1, wherein said insert receiving well is cylindrically shaped.

12. The brachytherapy device of claim 1, wherein the bottom of said insert receiving well comprises a pin capable of aligning said insert device.

13. The brachytherapy device of claim 12, wherein said pin is conically shaped.

14. The brachytherapy device of claim 1, wherein the bottom of said insert receiving well comprises multiple pins capable of aligning said insert device.

15. The brachytherapy device of claim 1, wherein said bottom surface comprises a hollow bottom.

16. The brachytherapy device of claim 1, wherein at least a portion of said hollow bottom is positioned underneath said staging area surface.

17. The brachytherapy device of claim 1, wherein the angle of said staging area with respect to a flat surface is less than 60 degrees when said bottom surface rests on said flat surface.

18. The brachytherapy device of claim 1, wherein the angle is of said staging area with respect to a flat surface is between 80 and 10 degrees when said bottom surface rests on said flat surface.

19. The brachytherapy device of claim 1, wherein the angle of said staging area with respect to a flat surface is between 60 and 30 degrees when said bottom surface rests on said flat surface.

20. The brachytherapy device of claim 1, wherein said one or more seed holder supports are capable of restricting longitudinal movement of said seed holder.

21. The brachytherapy device of claim 1, wherein said one or more seed holder supports are capable of restricting latitudinal movement of said seed holder.

22. The brachytherapy device of claim 1, wherein said loading area comprises a restraining wire attached to said one or more seed holder supports, wherein said restraining wire is capable of restricting axial movement of said seed holder.

23. The brachytherapy device of claim 1, wherein said staging area comprises a top portion and a bottom portion, wherein said bottom portion comprises a trough capable of collecting a radioactive seed that rolls down said top portion.

24. The brachytherapy device of claim 1, wherein said lid is attached to said body via an integral hinge.

25. The brachytherapy device of claim 1, wherein said lid defines an interior region, wherein a portion of said interior region comprises a protrusion capable of restraining movement of a seed holder within said insert device when said lid is closed.

26. The brachytherapy device of claim 25, wherein said protrusion extends between the pick-up handles of said insert device when said lid is closed.

27. The brachytherapy device of claim 25, wherein the clearance between said protrusion and said seed holder is less than 0.1 inches.

28. The brachytherapy device of claim 25, wherein the clearance between said protrusion and said seed holder is less than 0.01 inches.

29. The brachytherapy device of claim 25, wherein the clearance between said protrusion and said seed holder is less than 0.005 inches.

30. The brachytherapy device of claim 1, wherein said brachytherapy device comprises a handle attached to said body.

31. The brachytherapy device of claim 30, wherein said handle comprises a lock that locks said lid in the closed position.

32. The brachytherapy device of claim 31, wherein said lock locks said lid in the closed position when said handle is in a vertical position.

33. The brachytherapy device of claim 30, wherein movement of said handle from a vertical position toward a horizontal position moves said lid from a closed position to an opened position.

34. The brachytherapy device of claim 30, wherein the center of gravity of said brachytherapy device is such that said lid closes from an open position when said brachytherapy device is lifted by said handle.

35. The brachytherapy device of claim 1, wherein said body and lid are aluminum.

36. A brachytherapy device comprising:
   a) an insert device comprising:
      i) multiple seed holder pockets, wherein each of said multiple seed holder pockets is capable of holding a seed holder, and
      ii) a pick-up handle;
   b) a body comprising a top surface, a bottom surface, and a staging area surface, wherein said top surface comprises an insert receiving well capable of holding said insert device, and wherein said staging area surface slopes away from said top surface and toward said bottom surface, and wherein said staging area surface comprises a loading area having one or more seed holder supports capable of holding a seed holder; and
   c) a lid attached to said body, wherein said lid is capable of opening to expose said insert receiving well and is capable of closing over said top surface to cover said insert receiving well.

37. The brachytherapy device of claim 36, wherein a connector connects at least two of said multiple seed holder pockets.

38. The brachytherapy device of claim 36, wherein each of said multiple seed holder pockets comprises a top portion and a bottom portion, wherein said top portion comprises a cylindrical inner space, and wherein said bottom portion comprises a rectangular inner space.

39. The brachytherapy device of claim 36, wherein said insert device comprises at least two pick-up handles.

40. The brachytherapy device of claim 39, wherein each of said at least two pick-up handles comprises an aperture.

41. The brachytherapy device of claim 36, wherein said insert device is plastic.

42. The brachytherapy device of claim 36, wherein each of said multiple seed holder pockets is capable of holding a seed holder having a rectangular shaped body.

43. The brachytherapy device of claim 30, wherein at least one of said multiple seed holder pockets comprises a vent.

* * * * *

UNITED STATES PATENT AND TRADEMARK OFFICE
CERTIFICATE OF CORRECTION

PATENT NO. : 6,639,237 B2
DATED : October 28, 2003
INVENTOR(S) : Laust Pedersen et al.

It is certified that error appears in the above-identified patent and that said Letters Patent is hereby corrected as shown below:

Column 16,
Line 44, please delete "30" and insert -- 36 -- therefor.

Signed and Sealed this

Fifteenth Day of February, 2005

JON W. DUDAS
*Director of the United States Patent and Trademark Office*